United States Patent
Zierhofer et al.

(10) Patent No.: US 8,938,304 B2
(45) Date of Patent: Jan. 20, 2015

(54) COCHLEAR IMPLANT POWER SYSTEM AND METHODOLOGY

(75) Inventors: Clemens M. Zierhofer, Kundl (AT); Ingeborg J. Hochmair, Axams (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 37 days.

(21) Appl. No.: 13/589,548

(22) Filed: Aug. 20, 2012

(65) Prior Publication Data

US 2012/0316618 A1    Dec. 13, 2012

Related U.S. Application Data

(62) Division of application No. 11/761,475, filed on Jun. 12, 2007, now Pat. No. 8,280,522.

(60) Provisional application No. 60/813,238, filed on Jun. 13, 2006.

(51) Int. Cl.
*A61N 1/378* (2006.01)
*A61N 1/36* (2006.01)
*A61N 1/372* (2006.01)

(52) U.S. Cl.
CPC ........ *A61N 1/36032* (2013.01); *A61N 1/37223* (2013.01); *A61N 1/3787* (2013.01)
USPC .......... 607/55; 607/56; 607/57; 607/59; 607/61; 607/136; 607/137; 607/149

(58) Field of Classification Search
USPC .......... 607/55–57, 59, 61, 136–137, 149
See application file for complete search history.

(56) References Cited

U.S. PATENT DOCUMENTS

| | | | |
|---|---|---|---|
| 4,357,497 A | 11/1982 | Hochmair et al. | 179/107 E |
| 4,428,377 A | 1/1984 | Zollner et al. | 128/419 R |
| 5,571,148 A * | 11/1996 | Loeb et al. | 607/57 |
| 5,733,313 A | 3/1998 | Barreras, Sr. et al. | 607/33 |
| 6,067,474 A * | 5/2000 | Schulman et al. | 607/57 |

(Continued)

FOREIGN PATENT DOCUMENTS

| | | | |
|---|---|---|---|
| EP | 2609959 | 7/2013 | A61N 1/36 |
| EP | 2609960 | 7/2013 | A61N 1/36 |

(Continued)

OTHER PUBLICATIONS

Jeutter "A Transcutaneous Implanted Battery Recharging and Biotelemetry Power Switching System", IEEE Transactions on Biomedical Engineering, vol. BME 29, No. 5, May 1982.

(Continued)

*Primary Examiner* — Christopher D Koharski
*Assistant Examiner* — Natasha Patel
(74) *Attorney, Agent, or Firm* — Sunstein Kann Murphy & Timbers LLP

(57) ABSTRACT

A cochlear implant system has an implantable portion that includes a stimulator module for producing for the auditory system of a user an electrical stimulation signal representative of an acoustic signal. The implantable portion further includes a battery for supplying power to the stimulator module, a receiver module for receiving an electrical power signal across the skin of a user, and a recharge module that uses the electrical power signal to recharge the battery. The recharge module recharges the battery at less than the maximum recharge rate.

8 Claims, 2 Drawing Sheets

(56) References Cited

U.S. PATENT DOCUMENTS

| | | | |
|---|---|---|---|
| 6,178,353 B1 | 1/2001 | Griffith et al. | 607/61 |
| 6,308,101 B1 | 10/2001 | Faltys et al. | 607/57 |
| 6,542,777 B1* | 4/2003 | Griffith et al. | 607/57 |
| 6,553,263 B1 | 4/2003 | Meadows et al. | 607/61 |
| 6,556,870 B2 | 4/2003 | Zierhofer et al. | 607/57 |
| 6,810,289 B1 | 10/2004 | Shaquer | 607/57 |
| 7,289,639 B2* | 10/2007 | Abel et al. | 381/312 |
| 8,280,522 B2 | 10/2012 | Zierhofer et al. | 607/61 |
| 2001/0031996 A1* | 10/2001 | Leysieffer | 607/57 |
| 2003/0191504 A1 | 10/2003 | Meadows et al. | 607/33 |
| 2004/0044389 A1 | 3/2004 | Crawford | 607/116 |
| 2005/0077872 A1 | 4/2005 | Single | 320/114 |
| 2005/0159791 A1 | 7/2005 | Daly et al. | 607/57 |
| 2006/0184213 A1* | 8/2006 | Griffith | 607/60 |

FOREIGN PATENT DOCUMENTS

| | | | |
|---|---|---|---|
| EP | 2609961 | 7/2013 | A61N 1/36 |
| WO | WO 01/39830 | 6/2001 | A61N 1/36 |
| WO | WO 2007/146908 | 12/2007 | A61N 1/36 |

OTHER PUBLICATIONS

Wilson, et al. "Better speech recognition with cochlear implants," *Nature*, vol. 352, pp. 236-238, Jul. 1991.

International Searching Authority International Search Report—International Application No. PCT/US2007/070949, dated Oct. 24, 2007, together with Written Opinion of the International Searching Authority, 15 pages.

European Patent Office, Extended European Search Report—Application No. 13160386.2-1662, dated Jun. 4, 2013, 6 pages.

European Patent Office, Extended European Search Report—Application No. 13160391.2-1662, dated Jun. 5, 2013, 6 pages.

European Patent Office, Extended European Search Report—Application No. 13160396.1-1662, dated Jun. 5, 2013, 6 pages.

* cited by examiner

COCHLEAR IMPLANT POWER SYSTEM AND METHODOLOGY

CROSS REFERENCE TO RELATED APPLICATIONS

This application is a divisional of U.S. patent application Ser. No. 11/761,475 filed Jun. 12, 2007, entitled "Cochlear Implant Power System and Methodology," which in turn claims priority from U.S. provisional patent application Ser. No. 60/813,238 filed Jun. 13, 2006, entitled "Cochlear Implant Power System and Methodology." Each of these applications is hereby incorporated herein by reference, in its entirety.

TECHNICAL FIELD

The present invention relates to cochlear implants, and more particularly, to power system and methodology for a cochlear implant

BACKGROUND ART

Cochlear implants and other inner ear prostheses are one option to help profoundly deaf or severely hearing impaired persons. Unlike conventional hearing aids that just apply an amplified and modified sound signal, a cochlear implant is based on direct electrical stimulation of the acoustic nerve. Typically, a cochlear implant stimulates neural structures in the inner ear electrically in such a way that hearing impressions most similar to normal hearing are obtained.

More particularly, a normal ear transmits sounds as shown in FIG. 1 through the outer ear 101 to the eardrum 102, which moves the bones of the middle ear 103, which in turn excites the cochlea 104. The cochlea 104 includes an upper channel known as the scala vestibuli 105 and a lower channel known as the scala tympani 106, which are connected by the cochlear duct 107. In response to received sounds transmitted by the middle ear 103, the fluid filled scala vestibuli 105 and scala tympani 106 function as a transducer to transmit waves to generate electric pulses that are transmitted to the cochlear nerve 113, and ultimately to the brain.

Some persons have partial or full loss of normal sensorineural hearing. Cochlear implant systems have been developed to overcome this by directly stimulating the user's cochlea 104. A typical cochlear prosthesis essentially includes two parts: the speech processor and the implanted stimulator 108. The speech processor (not shown in FIG. 1) typically includes a microphone, a power supply (batteries) for the overall system and a processor that is used to perform signal processing of the acoustic signal to extract the stimulation parameters. In state-of-the art prostheses, the speech processor is a behind-the-ear (BTE-) device. The stimulator generates the stimulation patterns and conducts them to the nerve tissue by means of an electrode array 110 which usually is positioned in the scala tympani in the inner ear. The connection between speech processor and stimulator is usually established by means of a radio frequency (RF-) link. Note that via the RF-link both stimulation energy and stimulation information are conveyed. Typically, digital data transfer protocols employing bit rates of some hundreds of kBit/s are used.

One example of a standard stimulation strategy for cochlear implants is called "Continuous-Interleaved-Sampling strategy" (CIS), which was developed by B. Wilson (see, for example, Wilson B S, Finley C C, Lawson D T, Wolford R D, Eddington D K, Rabinowitz W M, "Better speech recognition with cochlear implants," Nature, vol. 352, 236-238, July 1991, incorporated herein by reference in its entirety).

The overall power budget of a contemporary cochlear prosthesis using an RF-link is essentially described by $$P_{BATT} = P_{SIG} \frac{P_{STIM}}{\eta}, \quad (1)$$

where $P_{BATT}$ is the power delivered by the battery, $P_{SIG}$ is the power consumption of the (external) signal processing, $P_{STIM}$ represents the power consumption of the implanted stimulator (including the actual electrical stimulation power), and $\eta$ is the overall power efficiency of the RF-link. The ratio $$\frac{P_{STIM}}{\eta}$$

represents the power flowing into the RF-transmitter. Note that $P_{STIM}$ and $P_{SIG}$ are first of all determined by the stimulation strategy used. For example, for CIS-strategy as described above, typical values are $P_{STIM}$=6 mW and $P_{SIG}$=6 mW. Assuming $\eta$=0.25 results in $P_{BATT}$=30 mW.

Totally Implantable Cochlear Implant (TICI)

A totally implantable cochlear implant (TICI) is a cochlear implant system without permanently used external components. A TICI typically includes a microphone and subsequent stages perform audio signal processing for the implementation of a particular stimulation strategy (e.g., CIS). It also includes stimulation electrodes, power management electronics, and a coil for the transcutaneous transmission of RF signals.

Unlike a pacemaker implant, the power supply of a TICI generally cannot be established by means of a non-rechargeable battery. This is because the overall pulse repetition rate of a TICI is much higher. For example, typically about 20 kpulses/s are generated by a cochlear implant using CIS, as compared to about 1 pulse/s in a pacemaker. Besides, a cochlear implant typically performs complex audio signal processing, as compared to simple sensing tasks performed in a pacemaker. Consequently, a rechargeable battery is typically required in a TICI, which needs recharging after a particular time period of operation. The external device used for charging includes equipment for the transcutaneous transmission of RF signals. It may be body worn and contain a second rechargeable battery and optionally other auxiliary devices like, without limitation, remote control, and FM-equipment.

Quick Charging

Recharging of an implanted rechargeable battery is conventionally achieved by means of an inductive RF-link. The standard approach, designated as "quick charging", involves charging up the battery as fast as possible, limited only by the maximum charging current. In typical state-of-the-art battery technologies (e.g., 3.6V Li-Ion technology), the absolute maximum charging current in mA is nominally equal to the capacity C. For example, for a battery with capacity C=20 mAh, the absolute maximum charging current is 20 mA, and thus it requires about 1 h to charge up an empty battery. However, the following aspects of quick charging need to be considered.

(a) The quick charging paradigm, i.e., long periods of slow discharge down to the lower energy limit and then a comparatively short period of recharge with maximum charging current up to the upper energy limit imposes considerable stress on the battery and might reduce numbers of charging cycles, before the battery looses its capacity. Typically only 500-1000 cycles for Li-Ion technology are obtained in such a mode. Assuming a battery capacity that is sufficient to operate the TICI for one day requires one charging session per day. For a maximum of 1000 cycles this means that after 3 years of implantation, the TICI, or at least the TICI rechargeable battery, may have to be replaced. However, a maximum period of only 3 years may be impractical for a wide variety of cochlear implant applications.

(b) The life time of the battery could be enhanced without increasing the maximum number of charging cycles by increasing the capacity. For example, if the capacity is sufficiently large to operate the TICI for 5 days instead of only one, then the maximum battery life time is also increased to about 15 years, which may be considered acceptable. However, increasing the capacity by a factor 5 also increases the volume of the capacity by the same factor, and this might be impossible with respect to the very limited space within a cochlear implant. Approaches to position an implanted rechargeable battery not in the local vicinity of the inner ear, but somewhere else in the body are technically feasible, but not currently implemented. For example, a rechargeable battery at the position of a pace maker device in the upper chest region may make sense from a technical point of view.

(c) Quick charging may increase the temperature of the battery and with it the temperature of the surrounding tissue. The amount of temperature rise can depend on many factors including magnetic strength RF-field, charging current, charging time, TICI mass, and blood circulation. A maximum temperature rise of 1K is tolerable.

(d) Assuming state-of-the-art battery technology, the maximum capacity for a rechargeable battery positioned in the local vicinity of the ear is limited to approximately tens of mAh. This limitation is due to space requirements and allows a TICI operation for about one day. However, from a patient point of view, the idea of a daily and obligatory charging session lasting for at least one or two hours often is not an attractive option.

Other Rechargeable Battery Considerations

An implanted rechargeable battery may not be appropriate in certain circumstances. For example, for very young children an implanted rechargeable battery may be too large or heavy. Various patients may not appreciate the idea of carrying a power source in the head, or the somewhat cumbersome (daily) recharging procedure.

SUMMARY OF THE INVENTION

In accordance with a first embodiment of the invention, a cochlear implant system has an implantable portion that includes a stimulator module for producing for the auditory system of a user an electrical stimulation signal representative of an acoustic signal. The implantable portion further includes a battery for supplying power to the stimulator module, a receiver module for receiving an electrical power signal across the skin of a user, and a recharge module that uses the electrical power signal to recharge the battery. The recharge module recharges the battery at less than the maximum recharge rate.

In related embodiments of the invention, the cochlear implant system may further include an external portion adapted for placement at a specific location on the external skin of a user. The external portion includes a power signal transmission module for transmitting the electrical power signal across the skin of a user; and a second battery for supplying power to the power signal transmission module. The second battery may be rechargeable. The external portion may be housed in a single enclosure and include a first magnet, with the implantable portion including a second magnet, wherein the external portion is adapted to be held in place on the user based substantially on the magnetic forces between the first magnet and the second magnet. Alternatively, or in combination with a magnetic force, the external portion may be held in place with other mechanisms known in the art, such as an ear hook.

In further related embodiments of the invention, the electrical power signal may be free of modulated programming data, or low-rate modulated programming data. The recharge module may recharge the battery at less than 50% or 10% the maximum recharge rate. The battery may power the stimulator module when the electrical power signal is not received by the receiver module. The recharge module may recharge the battery while the battery is supplying power to the stimulator module. The stimulator module may be adapted to be powered by the electrical power signal when the battery is non-operational. The stimulator module may include an electrode array; a microphone for receiving acoustic signals; and a signal processor for converting acoustic signals received by the microphone into the electrical stimulation signal representative of the acoustic signal. The signal processor stimulating the electrode array with the electrical stimulation signal. The receiver module may include a receiver coil for receiving the electrical power signal.

In accordance with another embodiment of the invention, a cochlear implant system includes an external portion adapted for placement at a specific location on the external skin of a user. The external portion includes a power signal transmission module for transmitting an electrical power signal across the skin of a user. The external portion further includes a battery for supplying power to the power signal transmission module. An implantable portion receives the electrical power signal and produces for the auditory system of the user an electrical stimulation signal representative of an acoustic signal. The implantable portion does not have a battery.

In accordance with related embodiments of the invention, the battery may be rechargeable. The external portion may be housed in a single enclosure, with external portion including a first magnet and the implantable portion including a second magnet. The external portion adapted to be held in place on the user based on the magnetic forces between the first magnet and the second magnet. The electrical power signal may be free of modulated programming data, or include low-rate modulated programming data.

In accordance with still further related embodiments of the invention, the implantable portion may include an electrode array; a microphone for receiving acoustic signals; and a signal processor for converting acoustic signals received by the microphone into the electrical stimulation signal representative of the acoustic signal. The signal processor stimulates the electrode array with the electrical stimulation signal. The implantable portion may include a receiver coil for receiving the electrical power signal, wherein the external portion includes a magnet for securing the external portion in a position adjacent the receiver coil.

In accordance with another embodiment of the invention, a method of operating a cochlear implant system is provided. The method includes receiving, by an implanted portion, an electrical power signal, the implantable portion including a battery having a maximum recharge rate. The battery is recharged at less than the maximum recharge rate using the electrical power signal.

In accordance with related embodiments of the invention, the electrical power signal may be transmitted across the skin of a user to the implanted portion. The electrical power signal may be free of modulated programming data, or include low-rate modulated programming data.

In accordance with further embodiments of the invention, an external portion may be provided that is adapted for placement at a specific location on the external skin of a user. The external portion may include a power signal transmission module for transmitting the electrical power signal across the skin of a user to the implanted portion; and a second battery for supplying power to the power signal transmission module. The method may further include recharging the second battery. The external portion may be housed in a single enclosure and include a first magnet, with the implantable portion including a second magnet. The external portion may be held in place on the user based substantially on the magnetic forces between the first magnet and the second magnet.

In still further embodiments of the invention, recharging the battery may include recharging the battery at less than 50% or 10% the maximum recharge rate. The battery may be used to power the implantable portion when the electrical power signal is not being received by the implanted portion. The electrical power signal may be used to simultaneously recharge the battery and provide operational power to the implantable portion so as to stimulate the auditory system of the user. Recharging the battery may consume less power than providing operational power. The electrical power signal may be used to power the implantable portion when the battery is non-operational. The implantable portion may produce an electrical stimulation signal representative of an acoustic signal. The implantable portion may include an electrode array, a microphone, and a signal processor, with the method further including at the signal processor, converting acoustic signals received by the microphone into the electrical stimulation signal representative of the acoustic signal, and stimulating the electrode array with the electrical stimulation signal. The implantable portion may include a receiver coil for receiving the electrical power signal, and the external portion a magnet, the method further comprising securing the external portion in a position adjacent the receiver coil using the magnet.

In accordance with another embodiment of the invention, a method of operating a cochlear implant includes providing an external portion adapted for placement at a specific location on the external skin of a user. The external portion includes a power signal transmission module for transmitting an electrical power signal across the skin of a user, and a first battery for supplying power to the power signal transmission module. The electrical power signal is received by an implanted portion that does not have a battery. The implanted portion produces an electrical stimulation signal representative of an acoustic signal.

In accordance with related embodiments of the invention, the electrical power signal may be free of modulated programming data, or include low-rate modulated programming data. The implantable portion may include an electrode array, a microphone, and a signal processor. The signal processor converts acoustic signals received by the microphone into the electrical stimulation signal representative of the acoustic signal, and stimulates the electrode array with the electrical stimulation signal. The implantable portion may include a receiver coil for receiving the electrical power signal, with the external portion including a magnet. The external portion is secured in a position adjacent the receiver coil using the magnet. The battery may be rechargeable. The external portion may be housed in a single enclosure, with the external portion including a first magnet and the implantable portion including a second magnet. The external portion is secured on the user based on the magnetic forces between the first magnet and the second magnet.

In accordance with another embodiment of the invention, a cochlear implant system includes an external portion adapted for placement at a specific location on the external skin of a user. The external portion includes a first magnet, and a power signal transmission module for transmitting the electrical power signal across the skin of a user to an implantable portion. The implantable portion has a second magnet. The external portion further includes a battery for supplying power to the power signal transmission module. The external portion is housed in a single enclosure, and is adapted to be held in place on the user based substantially on the magnetic forces between the first magnet and the second magnet.

In accordance with related embodiments of the invention, the battery may be rechargeable. The electrical power signal may be free of modulated programming data.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

In illustrative embodiments of the invention, a system and method for operating a cochlear implant includes an external component that includes a battery and a power transmission module. An implanted component receives an electrical power signal from the power transmission module, which is then used to power the implanted component while simultaneously recharging the implanted component's rechargeable battery in the background. Further embodiments of the invention are directed to a small "battery button" that may be advantageously used to supply power, but not modulated programming data, to an implanted cochlear component.
"Background Charging"

Figure 1:
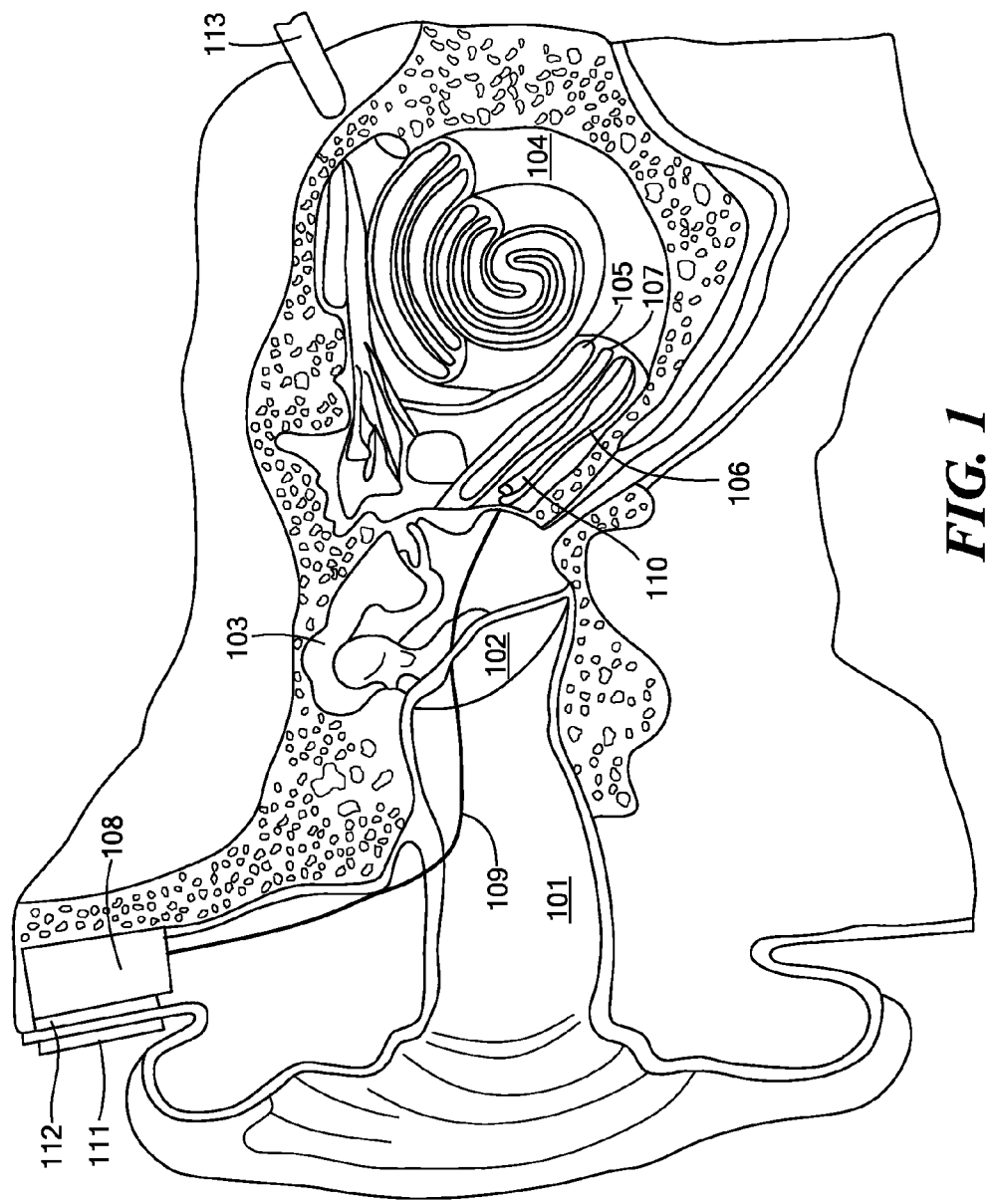
FIG. 1 shows the ear structure of a human ear and a typical cochlear implant system.
Figure 2:
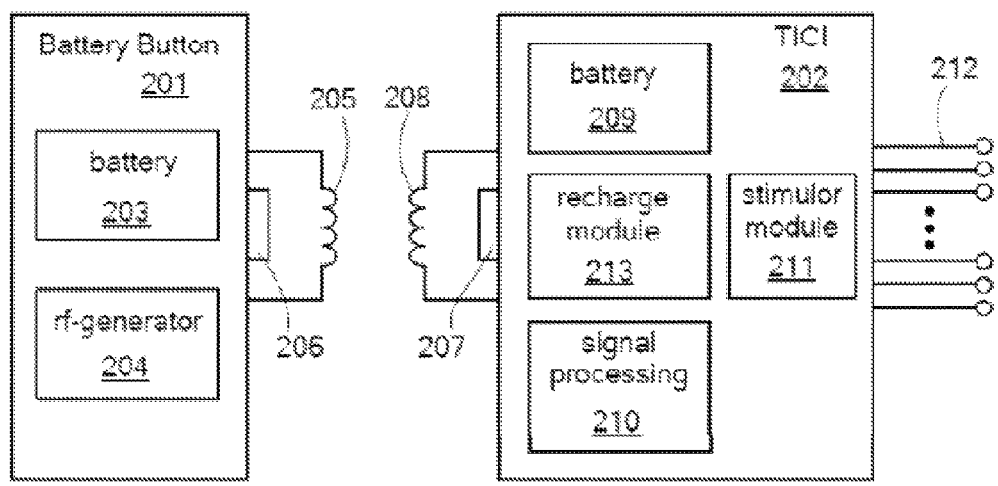
FIG. 2 is a block diagram showing a cochlear implant system that implements "background charging," in accordance with one embodiment of the invention.

FIG. 2 is a block diagram showing a cochlear implant system that implements "background charging," in accordance with one embodiment of the invention. "Background charging" may be used, for example, to charge a totally implantable cochlear implant (TICI). The external device 201 may be button-like (a "battery button"), containing an external battery 203, along with RF circuitry 204 and a transmitter coil 205 for generation and transmission of electrical power signals transmitter coil 205. The external device 201 may also contain a magnet 206, which in combination with a second implanted magnet 207 holds a minimal distance between transmitter and receiver coils 205 and 208, respectively. The external battery may be rechargeable.

In various embodiments, the external device 201 transmits power, but no or minimal information to the TICI. Minimal information may be, for example, low-rate programming data that is modulated onto the power signal. As used in this description and the accompanying claims, the term "low rate programming data" shall mean data transmitted at a rate of 1 kHz or less, unless the context otherwise requires.

The energy received in the TICI 202 (e.g., by receiver module 208, which illustratively is a coil) may be split up into two parts. The first portion of energy may be used to supply the TICI 202 with sufficient energy $P_{SIG}+P_{STIM}$ for normal operation, i.e., for signal processing 210 and for the generation by stimulator module 211 of stimulation signals that stimulate electrodes 212. A second portion of energy $P_{RECHARGE}$ is used by recharge module 213 to recharge the energy storing device 209. Since $P_{RECHARGE}$ will usually be considerably smaller than $P_{SIG}+P_{STIM}$, the concept is designated as "background charging".

The overall energy budget is given by $$P_{BATT} = \frac{1}{\eta_{cw}}(P_{SIG} + P_{STIM} + P_{RECHARGE}). \quad (2)$$

The main difference to Eq. (1) is that the RF-efficiency $\eta_{cw}$ can be substantially higher than $\eta$, since no data, but only CW signals are used. For example, assuming $P_{BATT}=30$ mW, $\eta_{cw}=0.5$, $P_{STIM}=6$ mW, and $P_{SIG}=6$ mW yields $P_{RECHARGE}=3$ mW.

Employing background charging, the TICI battery 209 is reloaded comparatively slowly. However, depending on the instantaneous loading state of the TICI battery 209, an operation without the external device 201 is possible. The periods $T_{RECHARGE}$ for background charging and $T_{OP}$ for TICI operation without the external device 201, i.e, when the TICI 202 is supplied with energy from the internal energy storing device, is governed by $$T_{RECHARGE}P_{RECHARGE}=T_{OP}(P_{SIG}+P_{STIM}). \quad (3)$$

This is valid as long as the amount of energy $T_{RECHARGE}P_{RECHARGE}$ is not limited by the capacity of the TICI battery. With the example of above, Eq. (3) yields $$T_{OP} = \frac{T_{RECHARGE}}{4}.$$

Some aspects of background charging are summarized in the following.

(a) The use of an external device that is worn by the user to slowly charge rechargeable battery 209 is somewhat contrary to a totally implantable system. However, the difference between background charging and quick charging is just a difference in quantity, but not in quality. Of course, when the external battery is not in use, the internal battery when sufficiently charged is capable of powering the stimulator module.

(b) Quick charging and background charging do not excluding each other. The implanted stimulator may be designed such that both recharging techniques are implemented in a practical manner.

(c) As compared to quick charging, obligatory charging sessions are not necessary with background charging.

(d) The external device, i.e., the battery button, used for background charging may be designed for maximum comfort for the patient. The components of the external device may be concentrated into a single enclosure which roughly has the size of an RF-transmitter as used in a contemporary cochlear implant system. In various embodiments, the external system may have no wires.

(e) For background charging, problems with battery cycle life time are very much relaxed. This is because of two reasons. First, the stress factor related with battery recharging is much lower because of the low charging current. Charging occur at less than the maximum charging rate of the battery. For example, the battery may be charged, without limitation, at 75%, 50%, 25%, or 10% its maximum charge rate. Second, because of the long charging time, the cycle periods are "naturally" much longer as compared to quick charging.

(f) Problems with respect to temperature development are minimized.

(g) Background charging can be reasonably implemented for almost every size of the battery capacity C. For example, even comparatively small capacities which permit a TICI operation without external device in the range of only one hour can be very much appreciated by the patients.

Figure 3:
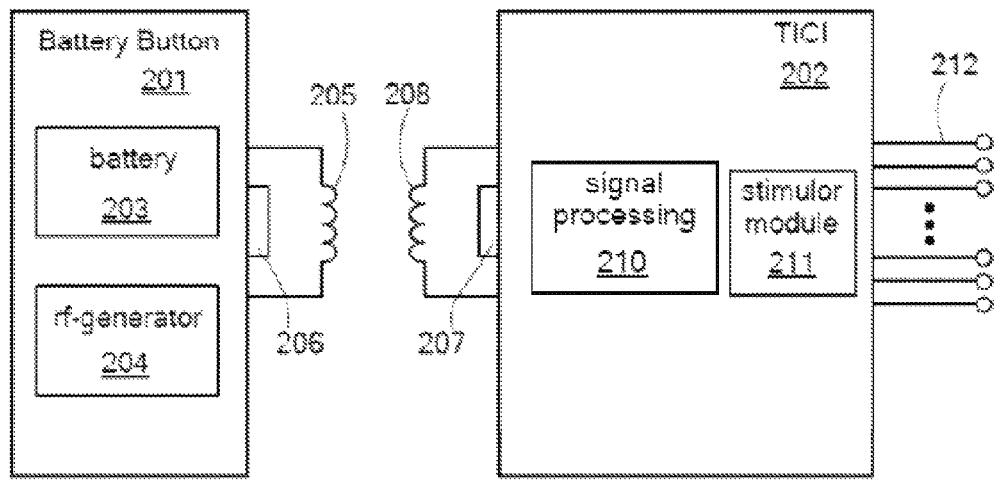
FIG. 3 is a block diagram showing a cochlear implant system without a battery in the implantable portion, in accordance with an embodiment of the invention.

(h) Note that a TICI even without an implanted rechargeable battery (C @ 0), but with other (possibly less effective) means to store electrical energy can be regarded as special cases for background charging. For example, the capacitors usually used to stabilize the implant supply voltage can be regarded as energy storing devices. The power supply power necessary to operate the TICI has to be provided by an external (rechargeable) battery. For example, not including the implantable rechargeable battery may be appropriate when a very small implant is needed, as for very young children. Additionally, various patients may not like the idea of carrying a power source in the head, or appreciate the somewhat cumbersome (daily) recharging procedure. FIG. 3 is a block diagram showing a cochlear implant system without a battery in the implantable portion, in accordance with an embodiment of the invention.

(i) An external battery may also be advantageously used with a TICI in cases where the implanted battery is non-functional (e.g. after its end of life) without considering a reimplantation. The external battery (i.e., a "button battery') may be used in such instances to power the stimulator module directly, without use of the implanted battery.

(j) One intrinsic advantage of background charging relates to the overall energy situation of the TICI. During the recharging period, there is an approximately constant energy flow to the TICI (cf. Eq. (2)). Within the TICI, the power consumption due to signal processing $P_{SIG}$ also is rather constant, but the stimulation power $P_{STIM}$ changes as a function of time, e.g., dependent on the loudness level. A power management system may be designed which aims at keeping the sum $P_{STIM}+P_{RECHARGE}$ constant. So the battery serves as an energy buffering system. For example, if $P_{STIM}$ is only 20% of the maximum consumption at a particular instant, the remaining 80% could be used to recharge the battery, instead of being wasted.

(k) In various embodiments, the battery button typically produces a continuous-wave (CW-) signal. As no data is modulated onto the transmitted energy, the external device 201 is advantageously simpler and cheaper than external devices of other cochlear implant systems. This is especially important for children.

(l) In various embodiments, the button 201 may be light enough to be held in place solely by magnetic force (i.e., the magnetic force between magnets 206 and 207) without exerting too much irritating pressure on the skin. Alternatively, or in addition to a magnetic force, other mechanisms may be used to hold the button in place, such as an ear hook. In preferred embodiments, the button weighs below approximately 10 to 12 g.

(m) Since the battery button can be manufactured relatively cheaply, several could be supplied with one implant.

(n) It is generally not necessary that the external battery of the button provide energy for a whole day, since the buttons can be exchanged easily. Since they can be made relatively cheaply, several of them are provided with one implant system.

Although various exemplary embodiments of the invention have been disclosed, it should be apparent to those skilled in the art that various changes and modifications can be made which will achieve some of the advantages of the invention without departing from the true scope of the invention.

What is claimed is:

1. A cochlear implant system comprising:
   an external portion adapted for placement at a specific location on the external skin of a user, the external portion including:
      a power signal transmission module for transmitting an electrical power signal across the skin of a user; and
      a battery for supplying power to the power signal transmission module; and
   an implantable portion that receives the electrical power signal and produces for the auditory system of the user an electrical stimulation signal representative of an acoustic signal, wherein the implantable portion does not have a battery,
   wherein the external portion does not transmit data to the implantable portion.

2. The cochlear implant system according to claim 1, wherein the battery is rechargeable.

3. The cochlear implant system according to claim 1, wherein the external portion is housed in a single enclosure, the external portion including a first magnet, the implantable portion including a second magnet, the external portion adapted to be held in place on the user based on the magnetic forces between the first magnet and the second magnet.

4. The cochlear implant system according to claim 1, wherein the implantable portion includes:
   an electrode array;
   a microphone for receiving acoustic signals; and
   a signal processor for converting acoustic signals received by the microphone into the electrical stimulation signal representative of the acoustic signal, the signal processor stimulating the electrode array with the electrical stimulation signal.

5. The cochlear implant system according to claim 1, wherein the implantable portion includes a receiver coil for receiving the electrical power signal, and wherein the external portion includes a magnet for securing the external portion in a position adjacent the receiver coil.

6. A method of operating a cochlear implant, the system including:
   providing an external portion adapted for placement at a specific location on the external skin of a user, the external portion including:
      a power signal transmission module for transmitting an electrical power signal across the skin of a user; and
      a first battery for supplying power to the power signal transmission module;
   receiving the electrical power signal with an implanted portion, wherein the implantable portion does not have a battery; and
   producing, by the implanted portion, an electrical stimulation signal representative of an acoustic signal,
   wherein the external portion does not transmit data to the implantable portion.

7. The method according to claim 6, wherein the implantable portion includes an electrode array, a microphone, and a signal processor, the method further comprising:
   at the signal processor, converting acoustic signals received by the microphone into the electrical stimulation signal representative of the acoustic signal, and stimulating the electrode array with the electrical stimulation signal.

8. The method according to claim 6, wherein the implantable portion includes a receiver coil for receiving the electrical power signal, and wherein the external portion includes a magnet, the method further comprising securing the external portion in a position adjacent the receiver coil using the magnet.

* * * * *